(12) United States Patent
Attariwala

(10) Patent No.: US 12,044,765 B2
(45) Date of Patent: Jul. 23, 2024

(54) PHANTOMS HAVING REFERENCE MEMBERS WITH MICROCHANNELS AND DIFFUSION WEIGHTED IMAGING USING SAME

(71) Applicant: Vigilance Health Imaging Network Inc., Montreal (CA)

(72) Inventor: Rajpaul Attariwala, Vancouver (CA)

(73) Assignee: VIGILANCE HEALTH IMAGING NETWORK INC., Montréal (CA)

( * ) Notice: Subject to any disclaimer, the term of this patent is extended or adjusted under 35 U.S.C. 154(b) by 1058 days.

(21) Appl. No.: 15/773,530

(22) PCT Filed: Nov. 6, 2015

(86) PCT No.: PCT/CA2015/051157
§ 371 (c)(1),
(2) Date: May 3, 2018

(87) PCT Pub. No.: WO2017/075690
PCT Pub. Date: May 11, 2017

(65) Prior Publication Data
US 2018/0335498 A1  Nov. 22, 2018

(51) Int. Cl.
*G01R 33/58* (2006.01)
*A61B 5/055* (2006.01)
*G01R 33/563* (2006.01)

(52) U.S. Cl.
CPC .............. *G01R 33/58* (2013.01); *A61B 5/055* (2013.01); *A61B 2560/0223* (2013.01); *A61B 2560/0228* (2013.01); *A61B 2576/00* (2013.01); *G01R 33/56341* (2013.01)

(58) Field of Classification Search
None
See application file for complete search history.

(56) References Cited

U.S. PATENT DOCUMENTS

| 4,499,375 A | 2/1985 | Jaszczak |
| 4,527,057 A | 7/1985 | Guyton et al. |
| (Continued) | | |

FOREIGN PATENT DOCUMENTS

| CN | 101991416 A | 3/2011 |
| CN | 102334991 A | 2/2012 |
| (Continued) | | |

OTHER PUBLICATIONS

English translation of Office Action for CN Application No. 201580085692.7, dated Apr. 3, 2020.
(Continued)

*Primary Examiner* — Shahdeep Mohammed
(74) *Attorney, Agent, or Firm* — Dorsey & Whitney LLP

(57) ABSTRACT

Apparatuses and methods for diffusion weighted imaging using phantoms are disclosed herein. An example phantom may include a reference member disposed within a housing, the reference member having a rod-like shape extending parallel to a long axis of the housing, the reference member formed from a material comprising a plurality of microchannels arranged longitudinally along at least a portion of the rod-like shape, and at least a portion of the housing may be formed to emulate a shape of a human torso.

22 Claims, 8 Drawing Sheets

(56) References Cited

U.S. PATENT DOCUMENTS

| | | | |
|---|---|---|---|
| 4,646,334 A * | 2/1987 | Zerhouni | A61B 6/508 378/207 |
| 5,165,050 A | 11/1992 | Goodenough | |
| 5,810,888 A * | 9/1998 | Fenn | A61K 41/0028 600/407 |
| 6,992,280 B2 | 1/2006 | White et al. | |
| 7,255,565 B2 | 8/2007 | Keegan | |
| 7,462,488 B2 | 12/2008 | Madsen et al. | |
| 7,965,080 B2 | 6/2011 | Breuer et al. | |
| 8,072,217 B2 | 12/2011 | Baldo et al. | |
| 8,535,061 B2 | 9/2013 | Boutchko et al. | |
| 8,666,133 B2 | 3/2014 | Vermandel et al. | |
| 8,814,572 B2 | 8/2014 | Eberler et al. | |
| 2009/0127451 A1 * | 5/2009 | Watson | A61B 6/583 378/207 |
| 2010/0066372 A1 | 3/2010 | Breuer et al. | |
| 2011/0043206 A1 * | 2/2011 | Kimura | G01R 33/56341 324/309 |
| 2011/0229055 A1 | 9/2011 | Clarke | |
| 2012/0068699 A1 | 3/2012 | Horkay et al. | |

FOREIGN PATENT DOCUMENTS

| | | |
|---|---|---|
| JP | 2011062508 A | 3/2011 |
| WO | 2015003271 A1 | 1/2015 |
| WO | 2017075690 A1 | 5/2017 |

OTHER PUBLICATIONS

English translation of Office Action for CN Application No. 201580085692.7, dated Nov. 25, 2020.
Rausch, J. et al., "Implementation of a Diffusion Tensor Imaging Phantom of the Lumbar Spinal Cord", ESMRMB Congress, Oct. 2015.
International Search Report and Written Opinion received for Canadian Patent Application V89767WO dated Jul. 25, 2016.
Fieremans, Els , "Validation Methods for Diffusion Weighted Magnetic Resonance Imaging in Brain White Matter",—Ch. 3: Design of anisotropic diffusion hardware fibre phantoms; Ph.D Thesis, Ghent University; Department of Electronics and Information Systems; Sep. 2008.
Pullens, et al., "Anisotropic Phantom for Diffusion Weighted MRI Applications", Instruction Manual, Brain Innovation bv, Maastricht, The Netherlands, Sep. 2011.
Extended European Search Report dated Jun. 7, 2019 for PCT application No. PCT/CA2015051157, 10 pages.
Translation of First Office Action dated Jun. 3, 2019 for Japanese application No. 2018-543413, 9 pages.
Krzyzak, Artur T. et al., "The b matrix calculation using anisotropic phantoms for DWI an DTI experiments*", Artur Tadeusz Krzyzak, et al., "The b matrix calculation using anisotropic phantoms for DWI an DTI experiments*," The National Centre for Research and Development for grant, 2015.
Rausch, et al., Rausch, et al., "Implementation of a diffusion tensor imaging phantom of the Lumbar Spinal cord", Magnetic Resonance Materials in Physics, Biology and Medicine, ESMRMB 2015, Sep. 2015, pp. S465-S467.
Watanabe, Makoto et al., "Flexible ex vivo phantoms for validation of diffusion tensor tractography on a clinical scanner", Makoto Watanabe, et al., "Flexible ex vivo phantoms for validation of diffusion tensor tractography on a clinical scanner," Radiat Med, Jun. 15, 2006, at 605-609.
Zhou, Feng-Lei et al., "Coaxially Electrospun Axon-Mimicking Fibers for Diffusion Magnetic Resonance Imaging", Feng-Lei Zhou, et al., "Coaxially Electrospun Axon-Mimicking Fibers for Diffusion Magnetic Resonance Imaging," ACS Applied Materials & Interfaces, Nov. 7, 2012, at 6311-6316.
English translation of Office Action dated Jul. 14, 2021 in connection with Chinese patent application No. 201580085692.7, 14 pages.
[English Translation] Notice of Preliminary Rejection mailed on Nov. 19, 2021 for Korean Patent Application No. 10-2018-7015935.
EP Exam Report dated Nov. 12, 2021 for EP Application No. 15 907 571.2-1126.
Buzzelli, Marc et al., "Initial Performance of the Diffusive Quantitative Imaging Phantom (DQIP): Thermal and SNR Characteristics Using a Clinical Protocol", Proceedings of the International Society for Magnetic Resonance in Medicine, vol. 22, Apr. 25, 2014, 2652.
Gatidis, Sergios et al., "Development of an MRI Phantom for Diffusion-Weighted Imaging with Independent Adjustment of Apparent Diffusion Coefficient Values and T2 Relaxation Times", Magnetic Resonance in Medicine. vol. 72, Oct. 2, 2013, pp. 459-463.
Hellerbach, Alexandra et al., "MRI Phantoms—Are There Alternatives to Agar?", Plos One. vol. 8, Issue 8, e70343, Aug. 5, 2013, pp. 1-8.

* cited by examiner

PHANTOMS HAVING REFERENCE MEMBERS WITH MICROCHANNELS AND DIFFUSION WEIGHTED IMAGING USING SAME

RELATED APPLICATIONS

This application is a U.S. National Stage filing under 35 U.S.C. § 371 of PCT Application No PCT/CA2015/051157 filed Nov. 6, 2015, which application is incorporated herein by reference, in it entirety, for any purpose.

TECHNICAL FIELD

Examples described herein relate to phantoms which may be used in diffusion weighted imaging and imaging techniques utilizing the same.

BACKGROUND

Diffusion weighted imaging (DWI) generally refers to imaging of particle diffusion (e.g. water molecule diffusion) in biological tissues. The imaging may be performed, for example, using a magnetic resonance imaging (MRI) device. DWI may be used to study and treat diseases, such as neurological disorders including stroke. Generally, diffusion at any given point in biological tissue may be restricted by the local environment, and therefore imaging of diffusion may provide an indication of the surrounding tissue properties at a microscopic level.

Since particles at a given spatial point in a patient can move to any other neighboring point within the biological tissue, imaging data obtained with DWI may contain not just a single displacement value but an entire three-dimensional (3D) distribution of displacement values. In principle, DWI images may contain at least six-dimensional data, compared to the usual 3D data of standard MRI images. This large set of data is difficult to display intuitively on a screen, and is time-consuming to acquire.

To reduce the dimensionality, diffusion data may be expressed as diffusion values, for example, apparent diffusion coefficients (ADC), which may be considered along a predetermined direction. ADCs may conventionally be a single scalar quantity and provide a measure of a diffusivity of a substance of interest, water for example, within a sample along a particular direction. Quantitative ADC values may aid a physician in determining if a particular biological tissue (e.g. organ) is behaving as expected or whether it is functioning abnormally. A tissue (e.g. organ) may have an associated ADC number indicating proper functioning. Non-conforming measurements may provide a basis for a diagnosis and/or treatment protocol.

SUMMARY

Example phantoms and diffusion weighted imaging using the same are disclosed herein. An example phantom may include a reference member disposed within a housing, the reference member having a rod-like shape extending parallel to a long axis of the housing, the reference member formed from a material comprising a plurality of microchannels arranged longitudinally along at least a portion of the reference member, and wherein at least a portion of the housing is formed to emulate a shape of a human torso.

An example apparatus may include a phantom. The phantom including a reference member disposed along a long axis of the phantom, the reference member comprising a plurality of hollow fibers, wherein the phantom is configured to be received by a magnetic resonance imaging apparatus.

An example imaging method may include obtaining diffusion-weighted images of a calibration phantom, wherein the calibration phantom is shaped as a human torso and includes at least one reference member extending a length of the phantom, the at least one reference member including a plurality of microchannels, determining diffusion values of the at least one reference member including the plurality of microchannels based on the diffusion-weighed images, and establishing a relationship between the determined diffusion values of the at least one member including the plurality of microchannels and modeled diffusion values of the at least one member including the plurality of microchannels.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

Figure 1:
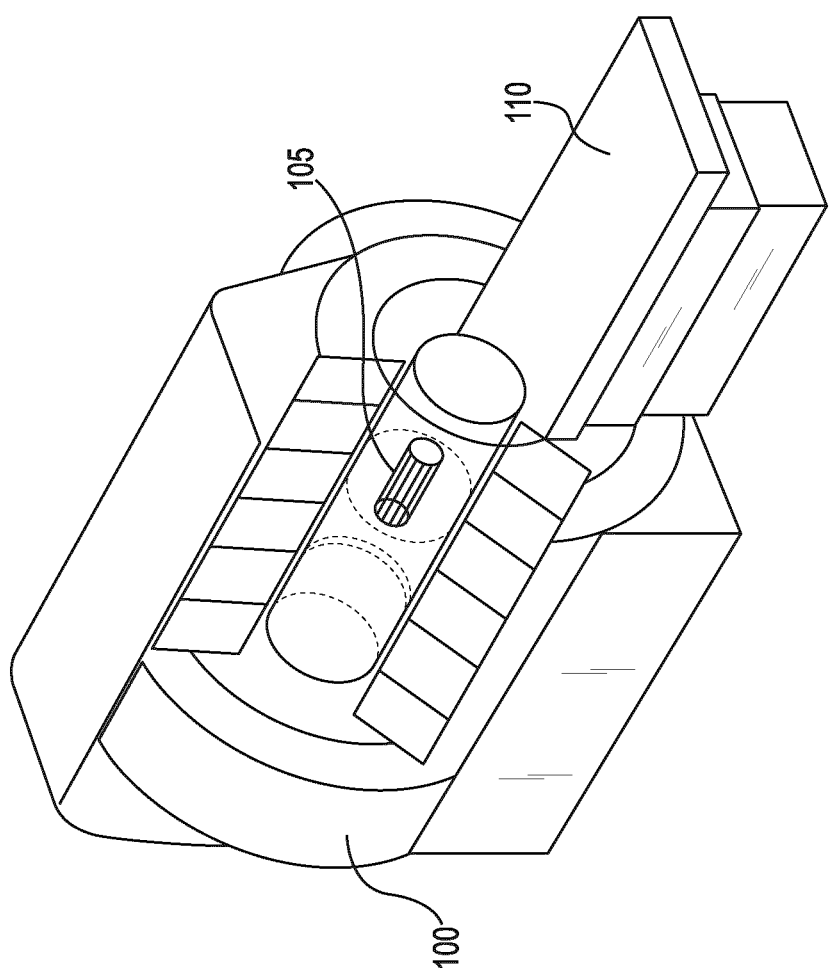
FIG. 1 is an imaging system arranged in accordance with an embodiment of the present disclosure.

all arranged in accordance with at least some embodiments of the present disclosure.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

This disclosure is drawn, inter alia, to methods, systems, products, devices, and/or apparatuses generally related to or using an imaging phantom that at least includes a reference member disposed within a housing. The reference member may have a rod-like shape extending along a long axis of the housing. The reference member may be formed from a material including a plurality of microchannels arranged longitudinally along at least a portion of the rod-like shape. The housing may be formed in a shape that emulates a human torso.

Some drawbacks to conventional DWI are discussed herein to facilitate appreciation of example phantoms and methods described herein. It is to be understood that the drawbacks are exemplary only, and examples of phantoms or methods described herein may not address all (or even any) of the described drawbacks. Drawbacks to conventional DWI may include various controllable and uncontrollable factors. One problem with quantitative DWI is that diffusion values depend not only on the structural properties of the tissue element being imaged, but also on the imaging conditions. Diffusion values, for example, may be expressed as apparent diffusion values (ADCs), which may be expressed as single scalar quantities and provide a measure of diffusivity within a sample along a particular direction. For example, different MRI units, imaging parameters, and temperature can affect ADC values. Another problem with DWI is that ADC values depend on not just the local diffusion characteristics, but also on macroscopic variations within the patient, such as changes in patient thickness. A point with a particular measured ADC value in the neck, for example, may give a different ADC value than a point with the same diffusion characteristics in the abdomen, e.g., the RF signals depend not only on the local tissues but also the macroscopic distribution of surrounding tissues including thickness and density.

Also, diffusion properties of different anatomical features may not be a simple function of density. The diffusion properties may be dependent upon the tissue architecture, particularly the intercellular spacing, anisotropy and tortuosity, e.g., twistedness, of the tissue.

To obtain quantitatively-useful ADC values, it may be desirable to calibrate the ADC values to compensate for the aforementioned problems. In examples of the present disclosure, a calibration phantom (which may also be referred to herein simply as a phantom), which comprises one or more reference members, may be used to calibrate an MRI device for obtaining diffusion weighted images. The diffusion characteristics of the reference members may be selected so that the ADC values of the reference members simulate ADC values of a desired anatomical feature. A phantom may be imaged prior to a patient scan, and the ADC values of the reference members of the phantom may be stored. A calibration curve of observed ADC values versus true ADC values, e.g., from modeled data, may then be used to convert measured ADC values of the patient scan to adjusted ADC values, which may compensate for unwanted effects such as temperature and scanner variations, for example.

In accordance with some examples described herein, a phantom comprising at least one reference member may be used in the determination of a diffusion image acquired by an MRI unit, so that the diffusion image more closely represents the diffusion characteristics of the tissues being imaged. As a result, the diffusion image may be used in an improved diagnosis of a disease, to define a treatment area, or make other medical decisions. Throughout the following descriptions and examples, the illustrative descriptions may be described in the context of calibrating diffusion weighted MRI images to generate quantitative diffusion values for diagnosis and/or treatment. However, it is to be understood that examples described herein may be applied to calibrating generally any imaging device that provides information related to diffusion within a patient.

FIG. 1 is an imaging system arranged in accordance with an embodiment of the present disclosure. The imaging system 100 may be implemented using an MRI machine and includes an imaging table 110. The imaging system 100 is depicted in FIG. 1 with a phantom 105 placed on the imaging table 110. The imaging system 100 may be used to obtain diffusion values of a patient and/or a phantom. An example diffusion value may be an apparent diffusion coefficient (ADC). The diffusion values of the phantom may be used to adjust diffusion values obtained of a patient.

In some examples, the phantom 105 may include a housing with one or more reference members disposed within the housing. The housing may have dimensions similar to a portion of a patient, such as a patient's torso. The dimensions may include heights, widths, and/or thicknesses. For example, the overall shape of the phantom 105 may have heights, widths, and thicknesses selected to match (e.g. approximate) those of a human torso. In some examples, the dimensions (e.g. heights, widths, and thicknesses) may be selected to match to a specific patient's torso. In some examples, the dimensions (e.g. heights, widths, and thicknesses) may be selected based on representative dimensions of a particular group of patients (e.g. all patients, patients in a particular age range, adult patients, child patients, patients of a particular ethnicity, and/or patients having a particular body mass index). In some embodiments, the diameter or other dimension of the phantom may vary with longitudinal position. For example a linear decrease from one end of the phantom to the other, such as to approximate the exterior surface of a human body, such as the shape of a torso or a head.

The reference members may be of sufficient size to be visible in diffusion images. The reference members may include a reference member that has a diffusion property selected to match a diffusion property (e.g. an anisotropic diffusion property) of one or more anatomical feature(s) (e.g. anatomical feature(s) of the human body). The reference members may be provided such that they match (e.g. approximate) the diffusion property of the anatomical feature(s) by, for example, providing microchannels in one or more of the reference members to match anisotropy of the anatomical feature(s). In some examples additionally or instead, a material making up the reference member may have a tortuosity provided or modified to match that of the anatomical feature(s). Generally the reference member may be provided to match any anatomical feature(s). Example anatomical features, include, but are not limited to the spinal cord, lung, liver, abdominal interface and stomach. In some examples, the phantom 105 may include reference members arranged to emulate multiple anatomical features. In some examples, the phantom 105 may include one or more reference members arranged to emulate a single anatomical feature.

In some embodiments, the anatomical feature may be the spinal cord. The spinal cord is prominent in many diffusion MRI images and runs through a significant length of the body. A reference member of the phantom 105 may be configured so that the diffusion properties of the reference member approximately match the diffusion properties of the spinal cord. In some embodiments, the reference member may include elongated channels, such as microchannels, that simulate the longitudinal isotropy, the radial anisotropy, and/or tortuosity of the spinal cord.

The phantom 105 may have one or more structural properties such as structural spacing, isotropy, anisotropy, and tortuosity, at various scales, such as at the cellular scale. Accordingly, feature in the phantom 105 may have structural properties which vary on the cellular scale.

In some embodiments, a reference member may have regions of inhomogeneity positioned and selected to match an anatomical feature. In some embodiments, a reference member may be formed to emulate a human spinal cord. To emulate the human spinal cord, the reference member may have longitudinal diffusion characteristics that are different than radial diffusion characteristics. For example, a reference member may extend the length of the phantom 105 and have a rod-like shape that is similar to a spinal cord and may further be formed from material that includes or produces microchannels that run at least a portion of the reference member.

During use, the phantom 105 may be placed on the imaging table 110 of the imaging system 100, which may be an MRI machine. The imaging system 100, in some embodiments, may measure diffusion properties of various molecules and elements, such as water, carbon-13, Fluorine-19, sodium-23, and/or phosphorous-31, to provide a few examples. In some embodiments, the room the imaging system 100 may be located and/or the phantom 105 may be controlled with regard to temperature, pressure, humidity, other environmental factors, and combinations thereof. In other embodiments, the environmental factors may be recorded and compared to reference conditions. After the phantom 105 has been placed in the imaging system 100, images of the phantom may be acquired and stored. The imaging system 100 and/or a computing system in communication with the imaging system 100 may calculate ADC values for the phantom 105, or at least one of the reference members included in the phantom 105.

Figure 2:
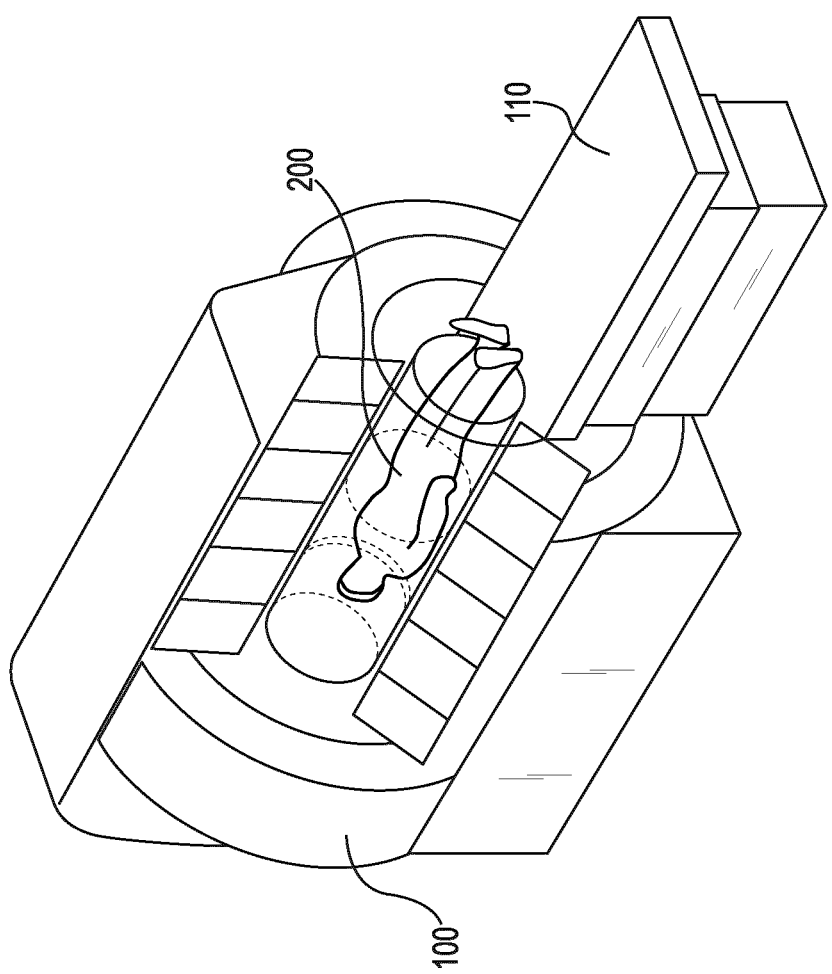
FIG. 2 is a view of the imaging system of FIG. 1 when obtaining a patient image in accordance with an embodiment of the present disclosure.

FIG. 2 is a view of the imaging system of FIG. 1 when obtaining a patient image in accordance with an embodiment of the present disclosure. FIG. 2 depicts the imaging system 100 of FIG. 1 having a patient 200 on the imaging table 110. The patient 200 may generally be any object for which the imaging system 100 may obtain images. The patient 200 may be, for example, a human, animal, or biological tissue. The imaging system 100, and/or a computing system in communication with the imaging system 100 may calculate ADC values for the patient 200. The imaging system 100 and/or a computing system in communication with the imaging system 100 may calculate ADC values for the patient 200, which values may be calculated and/or adjusted in accordance with the ADC values for the phantom 105 of FIG. 1.

Figure 3A:
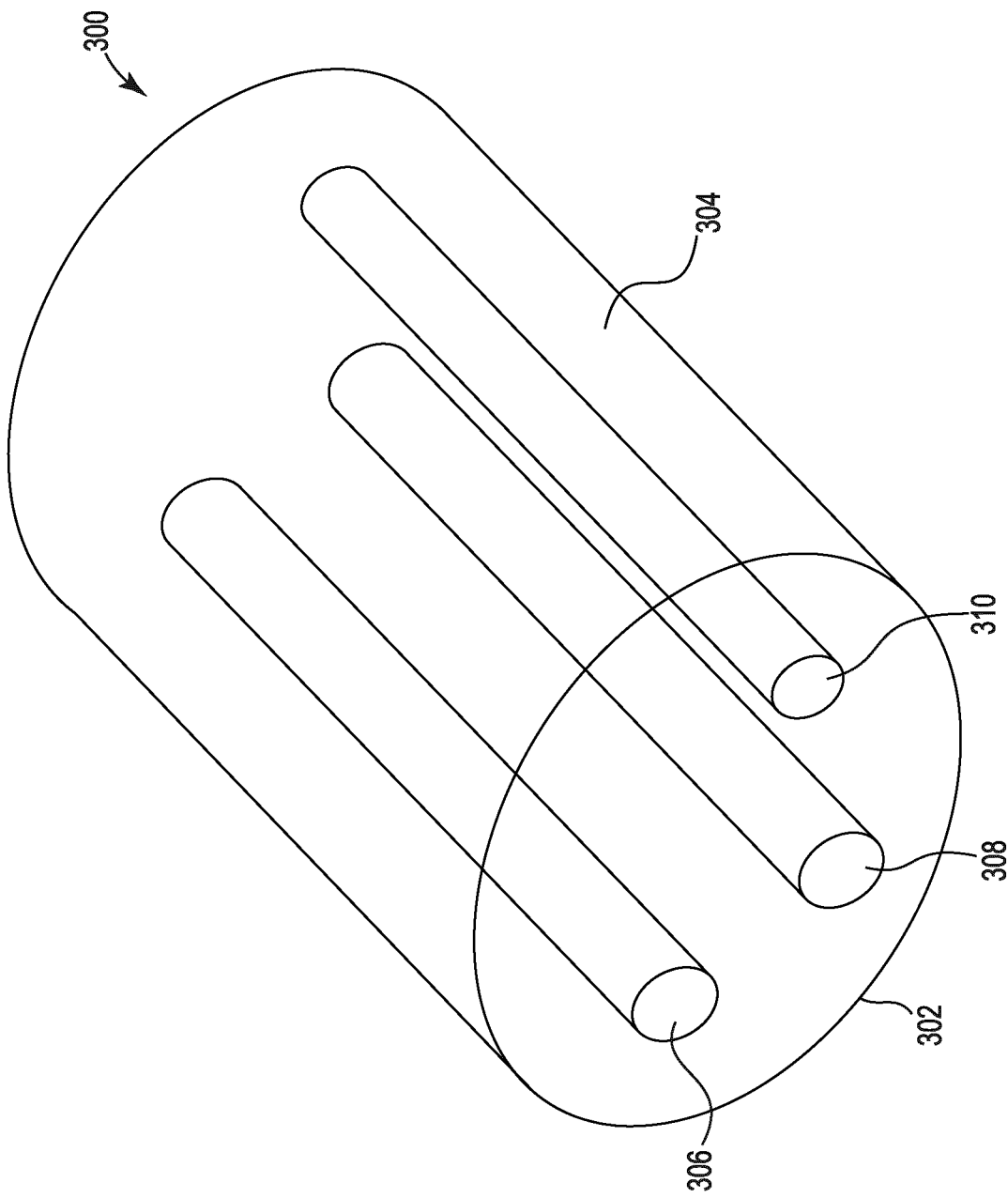
FIGS. 3A and 3B are schematic illustrations of a calibration phantom arranged in accordance with an embodiment of the present disclosure.
Figure 3B:
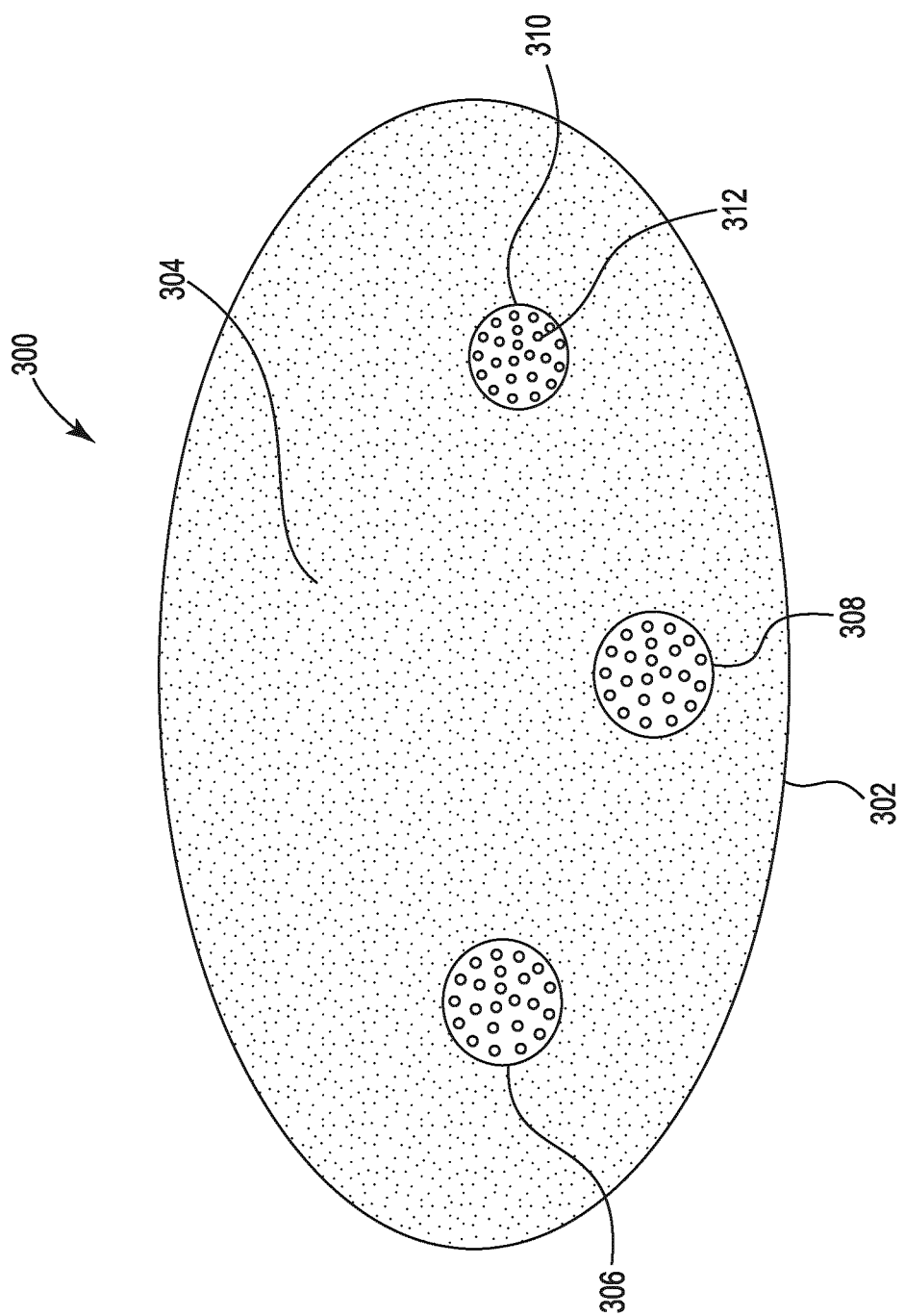

FIGS. 3A and 3B are schematic illustrations of a phantom arranged in accordance with an embodiment of the present disclosure. The phantom 300 may be implemented using the phantom 105 of FIG. 1. The phantom 300 includes a housing 302, three reference members 306, 308, and 310, and a fill material 304. Although, three reference members are shown, any number of reference members may be used, including 1, 2, 3, 4, 5, 6, 7, 8, 9, 10, or more reference members. The reference member(s) may emulate the tissue architecture of various anatomical features (e.g. mammalian organs and/or tissue). The phantom 300 may be used to calibrate DWI imaging, for example.

The housing 302 may be formed into the shape of a human torso, in some embodiments. Additionally, a phantom may be formed to mimic the shape and size of a patient's torso. In embodiments where the phantom's overall shape and size is shaped as a human torso, the location of the reference member(s) may be selected so to match (e.g. approximate) the relation a spinal cord has to the sides of the human torso. For example, the spinal cord may be closer to the back of the patient than to the front of the patient. As a consequence, the amount and type of tissue an MRI signal may propagate through to reach the spinal cord may be different for different directions. The difference in amount and type of material the signals may propagate may lead to different ADC measurements, which may need to be accounted for in a calibration sequence. Thus, by placing the reference member in a phantom, e.g. the reference member 308 of FIG. 3A closer to a back surface of the phantom 300 than a top surface of the phantom, the calibration images may better approximate human physiology and thus provide improved calibration data.

In some embodiments, the housing 302 may include other anatomical features in addition to being torso-shaped. For example, the housing 302 may include arms, a neck, a head, or combinations thereof. In some embodiments, the housing 302 may take the form of a whole body, either adult or child sized. In some embodiments, the size of the housing 302 may be adjusted to substantially match, or approximate, the size of a patient to be scanned. For example, the housing may include side portions that may fold in on themselves allowing the housing 302 to expand and contract a desired amount.

In some embodiments, the volume of the phantom 300 between the housing 302 and each of the reference members 306-310 may be filled with the fill material 304. The fill material 304 may have different diffusion characteristics than the reference members 306-310, and may mimic diffusion characteristics of various anatomical features. For example, the fill material 304 may be formed within the housing 302 and around the reference members 306-310, and may have variations in density throughout. In some embodiments, the fill material 304 may be formed from a material that mimics anatomical features other than a spinal cord, to mimic the various anatomical tissues that are between the spinal cord and the skin of a human, such as organs, fat, muscle, and bone. Examples of fill material 304 may include aqueous solution, gels, thickeners, expanded polymers filled with an aqueous solution. Example aqueous solutions may include water mixed with saline, or water mixed with glycerin, etc. In some embodiments, at least one of the reference members may be positioned within the phantom 300 to mimic the location of a spinal cord within a human torso. The reference member positioned to mimic the spinal cord may be formed along the entire length of the phantom 300 and may be rod-shaped.

In some embodiments, the fill material 304 may include multiple types of fill materials, with each fill material type separated by a partition. Each fill material type may be selected to emulate a different anatomical structure, such as bone, fat, muscle, tendon, or cartilage. In such an embodiment, at least one of the three reference members may run through all partitions so emulate a spinal cord, for example.

The reference member(s) may be formed from one or more materials. At least one of the materials may include thin core microchannels, e.g., hollow fibers. The microchannels may have inner diameters on the order of one micron (e.g. diameters ranging from 1-100 microns in some examples, 1-10 microns in some examples), to match (e.g. approximate) tissue architecture of the spinal cord. In some embodiments, the size of the microchannels may be selected to match the cell architecture of the brain. Further, at least one material of a reference member may be chosen to include different axial and/or radial diffusion characteristics, which may also match (e.g. approximate) the diffusion characteristics of anatomical feature(s), e.g. a spinal cord. Example materials include dialysis filters from dialysis tubes, which have diffusion characteristics similar to a spinal cord, e.g., different diffusion characteristics in a radial direction than in a longitudinal direction. In some examples, a reference member may include a cellulistic polymer such as a regenerated cellulose or a cellulose ester. In some examples, a reference member may include any kind of carbon tube, which can be grown to have tubes with diameters on the order of a cell membrane. In some embodiments, the spinal cord of a cadaver may be used.

A reference member may include a plurality of elongated tubes, the tube walls containing a fluid and diffusion within the fluid being restricted in a radial direction due to the tube walls. In some examples, a reference member may include a plurality of elongated members, such as rod or needle like structures. In some examples, a reference member may include a plurality of layers, such as polymer layers, which may be generally aligned in a parallel stacked arrangement. A reference member may include an anisotropic material, such as an aligned polymer, liquid crystal, and/or the like.

The reference members 306-310 may have different diffusion characteristics. The different diffusion characteristics may be due to variations in isotropy/anisotropy characteristics of the materials from which the reference members are formed, for example. The anisotropy characteristics of the materials may include uniaxial anisotropy (e.g. a first diffusion value for a particular direction, and a second diffusion value for any orthogonal direction), biaxial anisotropy (e.g. a first diffusion value for a particular direction, a second diffusion value for a particular orthogonal direction, and a third diffusion value for the other mutually orthogonal direction), and various other anisotropy characteristics anatomical feature(s) may display. In some examples, the reference members have different densities that approximate known anatomical features. In some examples, one or more reference members may emulate a human spinal cord and display longitudinal diffusion properties that are different than radial diffusion properties. In some embodiments, the one more members that emulate a human spinal cord may include microchannels that extend in a longitudinal direction of the member, e.g., hollow fibers that extend at least a portion of the reference member.

One of the reference members 306-310 may be formed from a polymer, such as a water-soluble polymer. An example water-soluble polymer may be polyvinylpyrrolidone (PVP), which may be homogeneous. Additional examples of water soluble polymers include coagulants, flocculants, amphoteric copolymers, and branched polymers, to name a few. Each reference member 306-310 may have a different percentage concentration of PVP, simulating different diffusion characteristics in different directions. In some embodiments, reference members may be selected to have regions of inhomogeneity from areas such as shoulder and lung as well as abdominal interfaces. In other embodiments, they are filled with liquid such as water, or with liquids of different viscosity. The reference members may be formed from materials that provide different diffusion characteristics in different directions within the material. For example, a reference member may be formed from a material that has a first diffusion value for an axial direction and a second diffusion value for a radial direction. In some examples, a reference material may be formed from a material that has different diffusion characteristics in more than two directions.

In some embodiments, the reference members 306-310 may be formed from materials such as rod bundles, fibrous materials, liquid crystals, stretched polymers, etc. These various other materials may provide different isotropy/anisotropy, and tortuosity characteristics. In some examples, the reference members may be formed from materials that form microchannels, or include microchannels, which may provide different diffusion values in different directions, such as radially and axially. For example, a rod bundle may form microchannels between the individual rods of the bundle. Other examples of materials that form or contain microchannels may include fibers, zeolites, solid porous polymers, and bamboo, to name a few. In some embodiments, the reference members 306-310 may be formed from a single piece of material that includes microchannels formed therein, with the microchannels forming hollow fiber type structures within the reference members.

FIG. 3B is a cross-sectional view of the phantom 300 in accordance with an embodiment of the present disclosure. The cross-sectional view of FIG. 3B shows an example of the location of the reference members 306-310 with relation to each other and to the housing 302. In the example of FIG. 3B, the reference member 308 may be positioned as a spinal cord would be in a human torso. The reference member 310 is shown to have microchannels 12 formed therein. The microchannels may mimic axons of a spinal cord, which may be characterized as hollow tubes that extend along at least a portion of the spinal cord. Axons may also display some tortuosity and have longitudinal diffusion characteristics that are different than a radial diffusion characteristic. Accordingly, the microchannels 312 may mimic spinal cord axons by having matched (e.g. approximate) diffusion characteristics.

The fill material 304 may have diffusion characteristics and densities that are different throughout the phantom 300. For example, the fill material 304 may be anisotropic. In some embodiments, the fill material 304 may be formed from an aqueous solution of different molecular weight water soluble polymers.

By providing a phantom that emulates a human torso that includes a simulated spinal cord, the phantom may provide an improved DWI reference for an imaging system, such as the imaging system 100 of FIG. 1.

Figure 4:
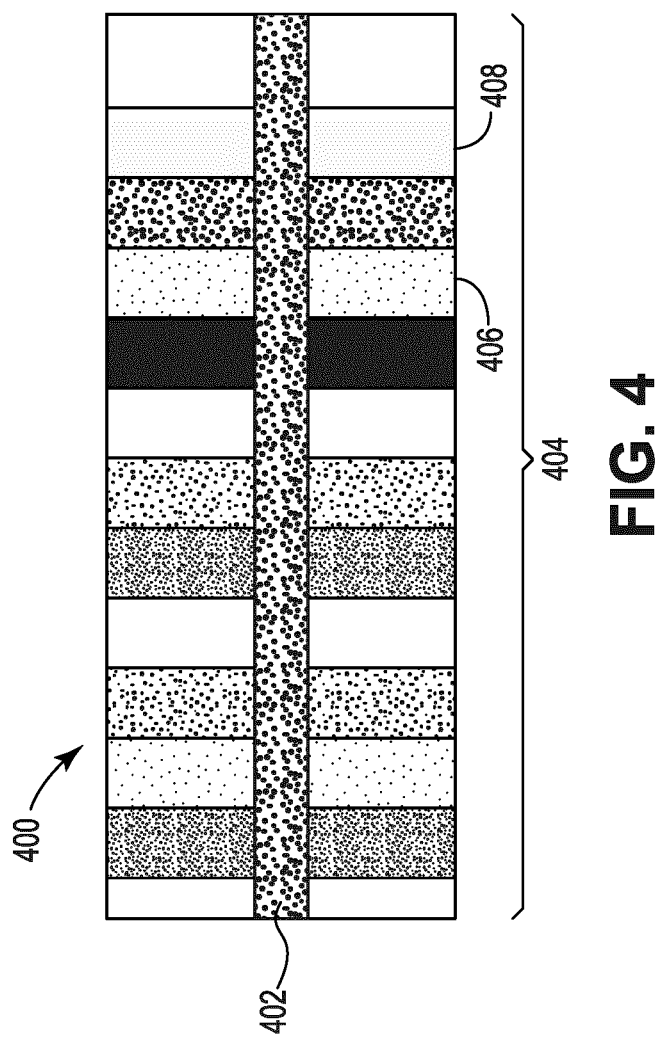
FIG. 4 is a schematic illustration of a calibration phantom arranged in accordance with an embodiment of the present disclosure.

FIG. 4 is an illustration of a phantom in accordance with an embodiment of the present disclosure. The phantom 400 includes a reference member 402 and a plurality of sections 404, including the section 406 and 408. The phantom 400 may be implemented using the phantom 105 of FIG. 1, for example, and may provide a calibration phantom for DWI.

The phantom 400 may include a reference member 402 and a plurality of slices 404 of fill material. The reference member 402 may emulate a human spinal cord, in some embodiments. In some embodiments, the plurality of sections 404 may be formed from different materials such that each section may have a different density. For example, the section 406 may be less, or more, dense than the section 408. By providing different densities by respective ones of the plurality of sections 404, the imaging of the phantom 400 may emulate different anatomical tissue densities around the reference member 402.

While the reference member 402 is shown to extend down the center of the sections 404, the location of the member 402 may be in other positions. For example, the reference member 402 may be positioned offset from a center axis of the sections 404 to simulate the location of a spinal cord within a human torso. Positioning the reference member 402 as such may more closely emulate a human torso not in just diffusion characteristics, but also in arrangement.

The plurality of sections 404 may take any shape, and may for example be shaped as circles, ellipses, wedges, or rectangles. In some embodiments, the sections 404 may mimic the shape of a human body. In some embodiments, the reference member 402 may be a cylindrical-like structure, e.g., rod-like, that extends throughout the phantom 500 from one end to the other, which may approximate the geometry of a spinal cord. In some embodiments, the each of the sections 404 and the reference member 402 may be formed from materials that have the same or similar diffusion anisotropy/isotropy and tortuosity as anatomical feature(s).

In some embodiments, individual ones of the plurality of sections 404 may be replaced with a section of a different size and/or diffusion characteristics. For example, a subset of the plurality of sections 404 may be replaced so that the phantom 400 emulates a torso of a shape and size of a patient to be scanned such that a "chest" area and a "belly" area of the phantom 400 approximates a patient. By replacing one or more of the plurality of sections 404, the overall size of the phantom 400 may be adjusted.

Figure 5:
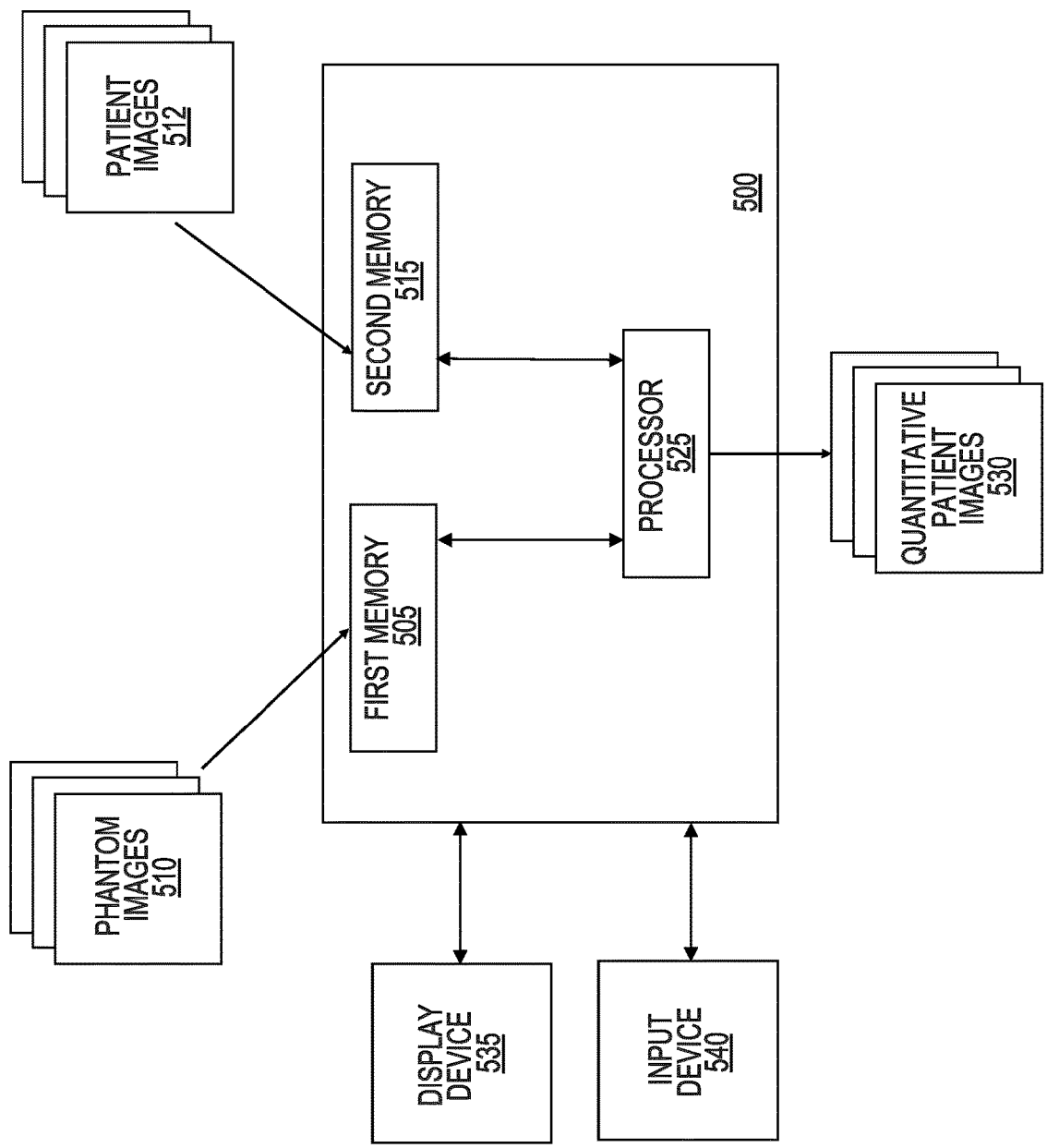
FIG. 5 is a schematic illustration of an apparatus arranged in accordance with an embodiment of the present disclosure.

FIG. 5 is a schematic illustration of an apparatus in accordance with an embodiment of the present disclosure. The apparatus 500 may be a portion of, an image processing component of, or in communication with, the imaging system 100 of FIG. 1, for example. The apparatus 500 includes a first memory 505, a second memory 515, a processor 525, phantom images 510, patient images 512, a display device 535, an input device 540, and quantitative patient images 530. While first and second memories are shown schematically, it is to be understood that these memories may be located on a same or on different memory devices, and that the data described as being stored in those memories may be distributed across any number of memory devices.

MRI pulse sequences may be used by imaging systems described herein and may be designed to measure a magnetic resonance (MR) signal, repeat the measurement a fraction of a second later, and use the difference to observe the changes due to diffusion. Magnetic field gradients may be measured parallel and perpendicular to one or more directions of anisotropy. The use of magnetic field gradients may allow the reconstruction of this signal at each point within the human body, and further depicts that various changes in diffusion with respect to various directions of the imaged structures. Image voxels, e.g., three-dimensional pixels, may often be expressed in terms of ADC values. As noted, the ADC values may be a scalar quantity describing the diffusion of a substance along a particular direction.

A limitation of conventional techniques may be that ADC values may be unduly influenced by scanner hardware variations, differences in pulse sequences, atmospheric variations (such as temperature, pressure and humidity), spatial position within the imager, patient thickness, patient density, and many other factors. Images are therefore not quantitative, e.g. the image voxels may be useful for qualitative variations in signal intensity, but may not present values representative of the actual diffusion characteristics of tissues within the patient. Some embodiments of the methods and apparatuses disclosed herein may overcome or address certain of these challenges and may provide more accurate calibration of diffusion images than presently available.

The first memory 505 may be used to store the phantom images 510, and second memory 515 may be used to receive and store patient images 512. All images may be received from an MRI imaging device, such as the imaging system 100 of FIG. 1, via wired or wireless communication. The apparatus 500 also includes a processor 525 that, based on the images and image statistics, may use methods described herein to adjust the patient images 512 and create new quantitative patient images 530.

In some embodiments, the processor 525 calculates the average and noise values of the voxels, e.g., 3D pixels, included in each of the phantom images 510 and/or patient images 512. The averages and values may be calculated from statistics within regions of interest (ROIs) defined in the images, which may be defined manually, semi-automatically, or automatically. Noise values may be important since they are affected by factors such as blood flow, layers of fat, and distance from the MRI coils to the ROIs. The noise values may be represented as standard deviation, variance, noise power spectra, Fourier components, principal components, independent components, texture properties, or any other metrics.

In some embodiments, the processor 525 may further control for the area, volume, and/or location of the reference members of a phantom, e.g., the phantom 105, 300, or 400. For example, a registration algorithm may be used to automatically compare the phantom images 510 that have been loaded into the first memory 505 to a model of the phantom, using for example a point-matching registration algorithm, a rigid registration algorithm, or a deformable registration algorithm. The model of the phantom may be stored in any memory accessible to the apparatus 500. In this manner, ADC measurements may be extracted by the processor 525.

The processor 525 may further establish a relationship between the statistics of the voxels of each member of the phantom images 510 and the known diffusion properties of each member as stored. In some embodiments, the relationship may be established by fitting one or more functional forms to the acquired data, such as a linear or quadratic equation. In other embodiments, correlation techniques, Bayesian inference, neural networks, machine learning algorithms or other algorithmic techniques may be used to form a relationship between the phantom images 510 stored in the first memory 505 and quantitative diffusion values. Once a relationship is established, the processor 525 may calculate correction factors to apply to the patient images 512 stored in the second memory 515. From the corrected images, the processor 525 may create quantitative images 530 that may be representative of diffusion characteristics associated with the patient images 512.

In some embodiments, the apparatus 500 may interact with a display device 535, such as a computer monitor, and an input device 540, such as a mouse and/or a keyboard.

In some embodiments, the second memory 515 may contain a series of axial 2D images that together form a full 3D representation of the patient based on one or more patient images 512. Each, or most, 2D image may contain an anatomical feature, such as a spinal cord. The processor 525 may modify each axial 2D image such that the spinal cord has the same image statistics as that of a reference member of a phantom based on the phantom images 510 stored in the first memory 505. The reference member images may have similar diffusion characteristics as the anatomical feature. For example, a patient image may be corrected such that the average ADC values of the spinal cord in each 2D image slice has the same ADC value as that of a reference member of a phantom described herein, where the reference member may have a matched (e.g. approximate) diffusion anisotropy as a spinal cord.

In practice, the phantom images 510 may be acquired as soon as possible before acquisition of the patient images 512, in a similar geometry, with the same MRI pulse sequences, and with a phantom that is as representative as possible of the patient being scanned. In other examples, time may elapse between the acquisition of phantom images and patient images, or vice versa.

In various embodiments, the processor 525 may be provided as either software, hardware, or some combination thereof. For example, the apparatus 500 may be implemented on one or more server-class computes, such as a PC having a CPU board containing one or more processors such as the Core i3, i5 or i7, or Xeon family of processors manufactured by Intel Corporation of Santa Clara, CA. The processor 625 may also include a main memory unit for storing programs and/or data relating to the methods described above. The memory (e.g. first and/or second memories 605 and/or 615) may include random access memory (RAM), read only memory (ROM), and/or FLASH memory residing on commonly available hardware such as one or more application specific circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other common storage devices.

For embodiments including a software program, the program may be written in any one of a number of high level languages such as FORTRAN, PASCAL, JAVA, C, C++, C #, LISP, PERL, BASIC or any suitable programming language. Additionally, the software could be implemented in an assembly language and/or machine language directed to the microprocessor resident on a target device.

Figure 6:
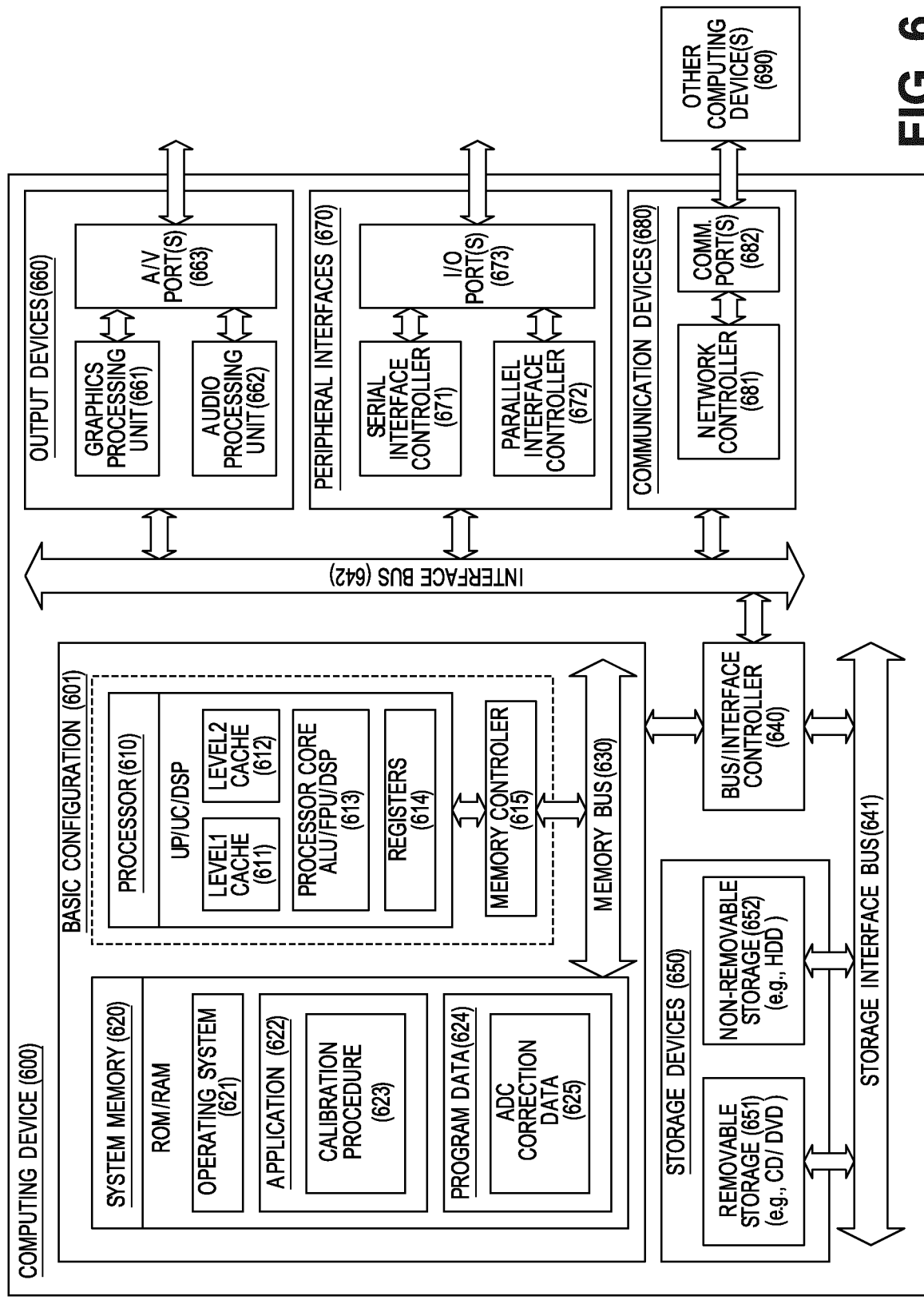
FIG. 6 is a block diagram illustrating an example computing device that is arranged for correcting ADC values from a patient based on ADC values of a reference phantom in accordance with the present disclosure.

FIG. 6 is a block diagram illustrating an example computing device 600 that is arranged for correcting diffusion values from a patient DWI based on diffusion values of a reference phantom in accordance with the present disclosure. In some embodiments, the diffusion values may be expressed as ADC values, but the expression of the diffusion value is non-limiting. In a very basic configuration 601, computing device 600 typically includes one or more processors 610 and system memory 620. A memory bus 630 may be used for communicating between the processor 610 and the system memory 620.

Depending on the desired configuration, processor 610 may be of any type including but not limited to a microprocessor (μP), a microcontroller (μC), a digital signal processor (DSP), or any combination thereof. Processor 610 may include one more levels of caching, such as a level one cache 611 and a level two cache 612, a processor core 613, and registers 614. An example processor core 613 may include an arithmetic logic unit (ALU), a floating point unit (FPU), a digital signal processing core (DSP Core), or any combination thereof. An example memory controller 615 may also be used with the processor 610, or in some implementations the memory controller 615 may be an internal part of the processor 610.

Depending on the desired configuration, the system memory 620 may be of any type including but not limited to volatile memory (such as RAM), non-volatile memory (such as ROM, flash memory, etc.) or any combination thereof. System memory 620 may include an operating system 621, one or more applications 622, and program data 624. Application 622 may include a calibration procedure 623 that is arranged to obtain ADC values from a phantom and correct the ADC values based on known, modeled data as described herein. Program data 624 may include patient ADC correction data 625, and/or other information useful for the implementation of obtaining quantitative ADC values of a patient DWI. In some embodiments, application 622 may be arranged to operate with program data 624 on an operating system 621 such that any of the procedures described herein may be performed. This described basic configuration is illustrated in FIG. 6 by those components within dashed line of the basic configuration 601.

Computing device 600 may have additional features or functionality, and additional interfaces to facilitate communications between the basic configuration 601 and any required devices and interfaces. For example, a bus/interface controller 640 may be used to facilitate communications between the basic configuration 601 and one or more storage devices 650 via a storage interface bus 641. The storage devices 650 may be removable storage devices 651, non-removable storage devices 652, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 620, removable storage 651 and non-removable storage 652 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of computing device 700.

Computing device 600 may also include an interface bus 642 for facilitating communication from various interface devices (e.g., output interfaces, peripheral interfaces, and communication interfaces) to the basic configuration 601 via the bus/interface controller 640. Example output devices 660 include a graphics processing unit 661 and an audio processing unit 662, which may be configured to communicate to various external devices such as a display or speakers via one or more A/V ports 663. Example peripheral interfaces 670 include a serial interface controller 671 or a parallel interface controller 672, which may be configured to communicate with external devices such as input devices (e.g., keyboard, mouse, pen, voice input device, touch input device, etc.) or other peripheral devices (e.g., printer, scanner, etc.) via one or more I/O ports 673. An example communication device 680 includes a network controller 681, which may be arranged to facilitate communications with one or more other computing devices 690 over a network communication link via one or more communication ports 682.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

Figure 7:
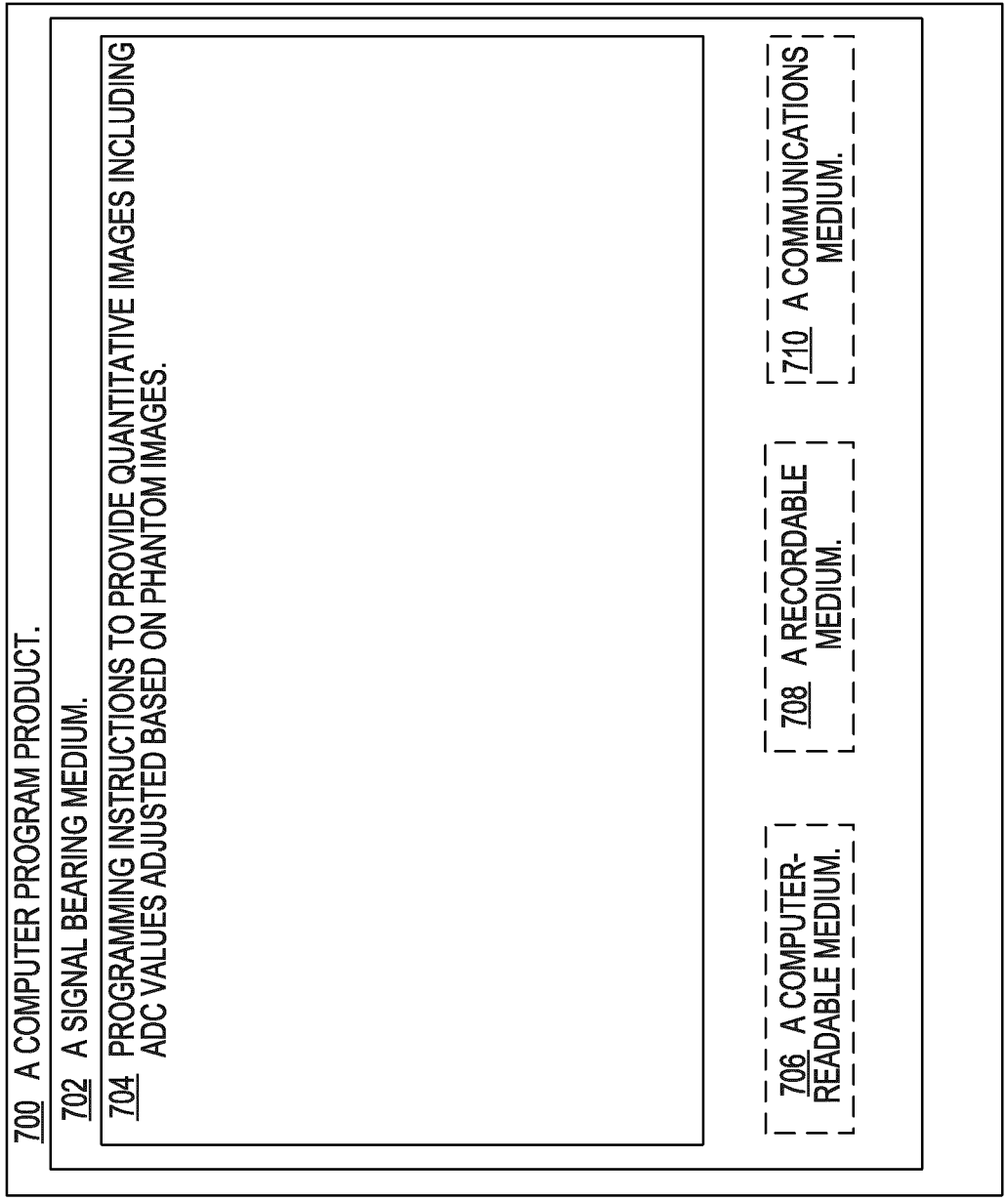
FIG. 7 is a block diagram illustrating an example computer program product that is arranged to store instructions for providing quantitative patient images in accordance with the present disclosure.

FIG. 7 is a block diagram illustrating an example computer program product 700 that is arranged to store instructions for providing quantitative patient images in accordance with the present disclosure. The signal bearing medium 702 which may be implemented as or include a computer-readable medium 706, a computer recordable medium 708, a computer communications medium 710, or combinations thereof, stores programming instructions 704 that may configure the processing unit to perform all or some of the processes previously described. These instructions may include, for example, one or more executable instructions for causing an imaging system, such as the imaging system 100, to provide quantitative patient images after adjusting their ADC values based on calibration ADC values, where the calibration ADC values are obtained from images of a phantom.

The present disclosure is not to be limited in terms of the particular examples described in this application, which are intended as illustrations of various aspects. Many modifications and examples can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. For example, if a user determines that speed and accuracy are paramount, the user may opt for a mainly hardware and/or firmware vehicle; if flexibility is paramount, the user may opt for a mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably countable", to each other to achieve the desired functionality. Specific examples of operably countable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. An imaging phantom for diffusion-weighted magnetic resonance imaging, the imaging phantom comprising:
   a housing having a cross-sectional area varying along a long axis of the housing to emulate a shape of a human torso;
   a first reference member disposed within the housing, the first reference member having a rod-like shape extending parallel to the long axis of the housing, the first reference member formed from a material comprising a plurality of microchannels arranged longitudinally along at least a portion of the reference member; and
   a fill material filling a volume of the imaging phantom between the housing and the first reference member, the fill material including a plurality of sections each having a different density, wherein the first reference member extends through the plurality of sections of the fill material.

2. The imaging phantom of claim 1, wherein respective ones of the plurality of sections of fill material are formed from materials having different diffusion characteristics.

3. The imaging phantom of claim 1, further comprising a second reference member, the second reference member having different diffusion characteristics than the first reference member.

4. The imaging phantom of claim 1, wherein the first reference member has a diffusion characteristic that is longitudinally isotropic and radially anisotropic.

5. The imaging phantom of claim 1, wherein the first reference member is formed from a plurality of polymer fibers.

6. The imaging phantom of claim 1, wherein at least one of the plurality of sections of fill material is detachable from the imaging phantom.

7. The imaging phantom of claim 1, wherein the fill material includes at least one of aqueous solution, gels, thickeners, or expanded polymer filled with an aqueous solution.

8. The imaging phantom of claim 1, wherein the reference member is positioned closer to one side of the housing to approximately match a position of a spinal cord in the human torso; and
    wherein the fill material is distinct from the housing and is configured to mimic bone surrounding the spinal cord.

9. An apparatus comprising:
    a phantom, wherein the phantom comprises:
    a reference member disposed along a long axis of the phantom, the reference member comprising a plurality of hollow fibers,
    a housing, wherein the reference member is disposed within the housing, wherein the housing has a cross-sectional area varying along the long axis of the phantom to emulate a shape of a human torso,
    a fill material filling a volume of the phantom between the housing and the reference member, the fill material including a plurality of sections each having a different density, wherein the reference member extends through the plurality of sections of the fill material, and
    wherein the phantom is configured to be received by a magnetic resonance imaging apparatus.

10. The apparatus of claim 9, wherein the reference member has a direction of elongation, and the plurality of hollow fibers are aligned with the direction of elongation.

11. The apparatus of claim 9, wherein the hollow fibers comprise a polymer.

12. The apparatus of claim 9, wherein the reference member includes a liquid.

13. The apparatus of claim 9, wherein at least one of the plurality of sections of fill material is detachable from the phantom.

14. A method comprising:
    obtaining diffusion-weighted magnetic resonance images of a calibration phantom, wherein the calibration phantom includes at least one reference member extending a length of the calibration phantom, the at least one reference member including a plurality of microchannels, wherein the calibration phantom includes a fill material filling a volume of the calibration phantom around the at least one reference member, the fill material including a plurality of sections each having a different density, wherein the reference member extends through the plurality of sections of the fill material, wherein a cross-sectional area of the calibration phantom varies along the length of the calibration phantom to emulate a shape of a human torso;
    determining diffusion values of the at least one reference member including the plurality of microchannels based on the diffusion-weighted magnetic resonance images; and
    establishing a relationship between the determined diffusion values of the at least one reference member including the plurality of microchannels and modeled apparent diffusion values of the at least one member including the plurality of microchannels.

15. The apparatus of claim 9, wherein the plurality of sections of fill material are disposed normally to the reference member.

16. The apparatus of claim 15, wherein each of the plurality of sections of fill material have a different diffusion characteristic.

17. The method of claim 14, wherein the fill material includes at least one of aqueous solution, gels, thickeners, or expanded polymer filled with an aqueous solution.

18. The method of claim 14, wherein establishing a relationship between the determined diffusion values of the at least one reference member including the plurality of microchannels and the modeled diffusion values of the at least one member including the plurality of microchannels comprises:
    comparing the determined diffusion values of at least the one reference member including the plurality of microchannels to the modeled diffusion values of the at least one member including the plurality of microchannels; and
    determining a statistical relationship between the determined diffusion values of the at least one reference member including the plurality of microchannels and the modeled diffusion values of the at least one member including the plurality of microchannels.

19. The method of claim 14, further comprising:
    obtaining diffusion-weighted images of a patient;
    determining diffusion values of the patient based on the diffusion-weighted images of the patient; and
    adjusting the diffusion values of the patient based on the relationship between the determined diffusion values of the at least one reference member including the plurality of microchannels and the modeled diffusion values of the at least one reference member including the plurality of microchannels.

20. The method of claim 14, wherein obtaining diffusion-weighted images of the calibration phantom comprises:
    transmitting a sequence of magnetic pulses through the calibration phantom;
    measuring the magnetic response of the calibration phantom after each pulse; and
    constructing the diffusion-weighted images of the calibration phantom based on the measured magnetic responses of the calibration phantom after each pulse.

21. The method of claim 14, wherein the diffusion values are apparent diffusion coefficient values.

22. The method of claim 14, further comprising:
    prior to obtaining the diffusion-weighted magnetic resonance images of the calibration phantom, replacing one of the plurality of sections of fill material with a replacement section of fill material, the replacement section of fill material having a different cross-sectional area than the one of the plurality of sections of fill material.

* * * * *